(12) United States Patent
Lee (10) Patent No.: US 12,085,310 B2
(45) Date of Patent: Sep. 10, 2024

(54) AIR PURIFIER

(71) Applicant: GONGGONG CO., LTD., Seoul (KR)

(72) Inventor: Sun Un Lee, Seoul (KR)

(73) Assignee: GONGGONG CO., LTD., Seoul (KR)

( * ) Notice: Subject to any disclaimer, the term of this patent is extended or adjusted under 35 U.S.C. 154(b) by 596 days.

(21) Appl. No.: 17/280,149

(22) PCT Filed: Aug. 6, 2019

(86) PCT No.: PCT/KR2019/009784
§ 371 (c)(1),
(2) Date: Mar. 25, 2021

(87) PCT Pub. No.: WO2020/071629
PCT Pub. Date: Apr. 9, 2020

(65) Prior Publication Data
US 2021/0341160 A1    Nov. 4, 2021

(30) Foreign Application Priority Data

Oct. 5, 2018    (KR) .................. 10-2018-0118613

(51) Int. Cl.
*F24F 3/16*    (2021.01)
*F24F 8/133*    (2021.01)
(Continued)

(52) U.S. Cl.
CPC .............. *F24F 8/133* (2021.01); *F24F 8/192* (2021.01); *F24F 13/28* (2013.01)

(58) Field of Classification Search
CPC .. F24F 8/133; F24F 8/192; F24F 13/10; F24F 13/28; A61L 9/122; A61L 2209/22;
(Continued)

(56) References Cited

U.S. PATENT DOCUMENTS

| 5,968,231 A | 10/1999 | Parmentier et al. |
| 2005/0011354 A1* | 1/2005 | Stead ................ B01D 46/10 |
| | | 95/218 |

(Continued)

FOREIGN PATENT DOCUMENTS

| EP | 1436090 B1 | 12/2006 |
| EP | 2436402 A1 | 4/2012 |

(Continued)

OTHER PUBLICATIONS

Extended European Search Report for Korean Application No. 19869571.0, Dated Aug. 5, 2022.

(Continued)

*Primary Examiner* — Frank M Lawrence, Jr.
(74) *Attorney, Agent, or Firm* — Robert C. Kowert; Kowert, Hood, Munyon, Rankin & Goetzel, P.C.

(57) ABSTRACT

The present disclosure relates to a double swirl type air purifier including: a main body configured to accommodate a liquid for purifying an inflow air; a suction part located at one side of the main body and configured to suction the inflow air; and a discharge part located at a predetermined position of the main body and configured to discharge an outflow air introduced from the main body. The main body includes a rotation part located at a lower portion of the main body and configured to rotate the liquid. A contact area between the liquid swirled by the rotation part and the inflow air swirled by inflow pressure of the suction part is increased so as to improve air purification efficiency.

7 Claims, 8 Drawing Sheets

(51) Int. Cl.
    *F24F 8/192*      (2021.01)
    *F24F 13/08*      (2006.01)
    *F24F 13/28*      (2006.01)

(58) Field of Classification Search
    CPC ... A61L 2209/134; Y02A 50/20; B01D 53/14;
                    B01D 53/18; B01D 53/185
    USPC ........ 96/257, 262, 269, 278, 281, 286, 287,
                96/301, 316, 317, 318, 321, 331, 332,
                                                96/333
    See application file for complete search history.

(56)            References Cited

U.S. PATENT DOCUMENTS

| 2006/0096460 | A1  | 5/2006  | Kim    |          |
| 2012/0093683 | A1  | 4/2012  | Hishida |          |
| 2018/0339258 | A1* | 11/2018 | Jeon ....................... | B05B 3/082 |
| 2022/0008861 | A1* | 1/2022  | Lin ....................... | B01D 47/02 |

FOREIGN PATENT DOCUMENTS

| JP | 2000-070643    | 3/2000  |
| JP | 2012-120720    | 6/2012  |
| KR | 10-2002-0056762 | 7/2002  |
| KR | 10-1569721     | 11/2015 |
| KR | 10-2017-0097363 | 8/2017  |

OTHER PUBLICATIONS

International Search Report from PCT/KR2019/009784, Date of mailing Nov. 12, 2019, pp. 1-2.

* cited by examiner

AIR PURIFIER

This application is a 371 of PCT Application No. PCT/KR2019/009784, filed Aug. 6, 2019, which claims benefit of Korean Patent Application No. 10-2018-0118613, filed on Oct. 5, 2018. The above applications are incorporated herein by reference. To the extent that any material in the incorporated application conflicts with material expressly set forth herein, the material expressly set forth herein controls.

TECHNICAL FIELD

The present disclosure relates to a double swirl type air purifier. More particularly, the present disclosure relates to a double swirl type air purifier in which, by providing a suction force for forcibly suctioning air in an inside of the air purifier together with a blowing force supplied at a predetermined pressure from an air inlet side of the air purifier, a primary swirl and a secondary swirl, each of which is generated when the air is mixed with water, are separately generated so as to increase the contact area between the water and the air, thereby improving efficiency of the air purifier.

BACKGROUND

The present disclosure relates to a double swirl type air purifier, and more particularly, to an improved double swirl type air purifier to enable more efficient and economical operation by reducing maintenance costs and improving performance.

In the modern society, the amount of fine dust in the air has increased rapidly due to various complex problems that pollute the air, such as industrial dust particles, automobile exhaust, and yellow dust, and the number of days in which the amount of fine dust contained in the air exceeds the recommended standard value has increased, which interferes with daily life and adversely affects human health due to heavy metals or the like contained in the fine dust.

When a window or the like is opened in order to ventilate dust or carbon dioxide dispersed by indoor activities in the home, contaminated fine dust containing heavy metals in the air enters the indoor space, thereby lowering the air quality of the indoor space. Thus, the number of patients with bronchial diseases, such as asthma, allergic bronchitis, and pneumonia, is increasing, and it is difficult to ventilate with ease even at home because it may cause problems in the health of sensitive people, such as children with underdeveloped physical growth or patients with bronchial diseases.

Accordingly, various types of air purifiers have been released and commercialized that are capable of collecting dust dispersed in the indoor air or harmful substances introduced from the outside, such as fine dust or dust containing heavy metals, dust particles, house ticks, mold, and viruses, so as to purify contaminated indoor air and discharge clean air to create a pleasant environment.

The air purifiers are devices that discharge clean air after purifying air containing pollutants such as fine dust particles, various harmful gases, various germs, mold, and viruses, and function to provide a pleasant and healthy environment by purifying air as well as removing various odors, fine particles such as mites, pollen, and pet hair.

These air purifiers may be largely classified into two types, namely, a dry type and a wet type. The dry type air purifiers may be further classified into an electric dust collection type and a filter filtration type.

The filter filtration type air purifier is configured to flow air through a filter so that various particles such as dust are filtered by the filter. However, there is a disadvantage in that maintenance costs such as periodic filter replacement are incurred. The electric dust collection type air purifier is not configured to use a filter, and thus has an advantage in that it is not necessary to change the filter. However, there are disadvantages in that, when dust accumulates on a dust collection plate, a removal ability of dust is weakened and a purification ability is reduced, and in that the electric dust collection type air purifier is ineffective at removing gases or odors other than dust.

As prior art, Korean Patent Laid-Open Publication No. 10-2014-0072928 discloses a wet type dust collector operated by a cyclone method as in the present disclosure, in which various harmful substances are removed by a wet method using water mist generated by high-pressure spray of cooling water, and at the same time, various foreign substances including fine dust are adsorbed by the water mist generated by the high-pressure spray of the cooling water, thereby finally being collected by the cyclone method. However, in the case of the prior art described above, the method is configured so that water and air are mixed with each other and swirled by a forced suction force. Thus, the method has a problem in that, since the contact time between the water and the air is short when passing through a guide part and first and second blades for forming a swirling flow, at the moment when a swirl is generated, some of the air is discharged as it is in the state in which harmful substances are not brought into contact with the water and thus a level of air purification is less than expected. Further, the air purifier is not suitable for home use because the noise generated in a process of suctioning air at a high speed and a high pressure is high.

In addition, the humidity of outflow air increases, which causes a need for dehumidification, and problems of hygiene and sterilization are also caused due to re-dispersion of humid pollutants. Moreover, a conventional technique using a disk increases the surface area by causing water droplets to be adsorbed on the disk. Therefore, when the disk is rotated at a high speed, spraying occurs, which causes problems due to high humidity and hygiene similar to those of a water spraying method. When the disk is rotated at a low speed, the contact area per unit time is small and thus efficiency is low.

A wet type air purifier is configured to purify air by bringing suctioned air into contact with a wet purifying agent such as water, and in this process, pollutants such as dust or gas are precipitated or dissolved. The wet type air purifier has advantages in that there is no need to change a filter and noise is low. Therefore, in recent years, the use of the wet type air purifier has gradually increased. However, in order to solve the problems described above, methods for miniaturization, noise reduction, and easy replacement of wet purifying agents or removal of deposits are required.

SUMMARY

The present disclosure has been conceived to solve the problems described above, and the present disclosure provides a double swirl type air purifier, in which, when suctioning air, an air swirl is generated in an inflow air and a liquid contained in the air purifier is swirled so that a contact area between air and liquid can be increased without a separate water spraying device, thereby removing impurities from the air more efficiently.

In addition, the present disclosure provides a more effective and convenient double swirl type air purifier that is simple in structure and convenient to manage since no filter or disk is provided.

Moreover, the present disclosure provides a double swirl type air purifier that, unlike a general centrifugal dust collector, contains liquid in a lower portion of the air purifier and does not need to suction inflow air at a high speed and high pressure, which enables the air purifier to be free from noise problems.

A double swirl type air purifier according to one embodiment of the present disclosure may include: a main body configured to accommodate a liquid for purifying an inflow air; a suction part located at one side of the main body and configured to suction the inflow air; and a discharge part located at a predetermined position of the main body and configured to discharge an outflow air introduced from the main body. The main body includes a rotation part located at a lower portion of the main body and configured to rotate the liquid. The contact area per unit time between the liquid swirled by the rotation part and the inflow air swirled by an inflow pressure of the suction part is increased so as to improve air purification efficiency.

In the double swirl type air purifier according to one embodiment of the present disclosure, the suction part may include an acceleration part disposed at an inlet of the suction part and configured to raise a speed of the inflow air such that an air swirl is generated.

In the double swirl type air purifier according to one embodiment of the present disclosure, the discharge part may include a guide part protruding from the discharge part toward an inside of the main body so as to prevent the inflow air and the outflow air from being mixed with each other.

In the double swirl type air purifier according to one embodiment of the present disclosure, the guide part may include an outflow air filter detachably fastened to the guide part so as to purify the outflow air introduced from the main body.

In the double swirl type air purifier according to one embodiment of the present disclosure, the main body may further include an electromagnetic force forming part disposed at a predetermined position of the main body. The electromagnetic force forming part may include one or more conductive wires or one or more magnetic materials being detachable from an inner wall of the main body and capable of forming an electric field or a magnetic field. Thus, formation of a dust film on a surface of the liquid is prevented by rapidly settling pollutants collected on the surface of the liquid surface into the liquid without stagnating on the surface of the liquid.

In the double swirl type air purifier according to one embodiment of the present disclosure, the main body may further include a cooling part located inside and/or outside the liquid accommodated in the lower portion of the main body and configured to lower a temperature of air inside the main body and/or a temperature of the liquid. A rate of collecting fine particles is improved by reducing a vapor pressure of the liquid and a repulsive force of the fine particles directed to the surface of the liquid from the inflow air.

In the double swirl type air purifier according to one embodiment of the present disclosure, the main body may further include one or more internal filters coupled to the main body and installed on an inner surface of the main body which is immersed within the liquid such that a re-dispersion of particles settled into the liquid is prevented.

In the double swirl type air purifier according to one embodiment of the present disclosure, the main body may further include a liquid suction part located at one side of a lower portion of an outer circumferential surface of the main body and configured to introduce the liquid, and a liquid discharge part located at the other side of the lower portion of the outer circumferential surface of the main body and configured to discharge the liquid containing impurities.

In the double swirl type air purifier according to one embodiment of the present disclosure, the suction part may include a cross-sectional area adjustment part being detachable from the suction part and configured to increase a speed of the inflow air and to lower a temperature of the inflow air. The cross-sectional area adjustment part may further include an air volume adjustment device configured to adjust a cross-sectional area of the suction port through which the inflow air passes such that a rate of collecting fine pollutants is improved by adjusting a moving speed of the inflow air or the outflow air and cooling down the inflow air or the outflow air.

In the double swirl type air purifier according to one embodiment of the present disclosure, the rotation part is configured to rotate at a low rotating speed or adjust a rotational force such that a center of the swirled liquid is not brought into contact with the rotation part. Thus, the double swirl type air purifier operates with low noise.

With the double swirl type air purifier of the present disclosure described above, it is possible to achieve the following effects.

The conventional technique using a disk requires a large amount of water because the disk has to be submerged in water, and is inconvenient to manage the disk. The double swirl type air purifier according to the present disclosure does not include a disk and has a large contact surface area of liquid per unit time compared to the weight of the liquid due to the formation of a swirl. Therefore, the air purifier is light and has excellent performance compared to the weight thereof, it is easy to lighten, miniaturize, and enlarge the air purifier, and it is convenient to maintain the air purifier due to a simple structure of the air purifier.

When the inflow air is not swirled, a relatively high pressure is formed on the surface of the liquid swirl so that there is a high possibility that the inflow air escapes without bringing the inflow air into contact with the surface of the liquid swirl. However, when the inflow air is swirled, since the swirled inflow air comes into contact with the liquid swirl along a descending flow path in a spiral direction, it is possible to achieve a large contact area and a lengthy contact time, and primary centrifugation occurs due to the swirl of the inflow air. Therefore, heavy particles come into contact with the surface of the liquid, such that the rate of collecting particles is high. Ekman suction generated by the liquid swirl lowers the contact surface and prevents collected foreign substances from stagnating on the contact surface. Since a purity of the surface is highly maintained due to the centrifugation effect of the liquid swirl, collection efficiency is constantly maintained, regardless of a contamination level of the liquid. Since adsorption of foreign substances and natural vaporization occur on the surface of the liquid, once foreign substances are adsorbed, a re-dispersion possibility of the foreign substances is very low. Since the adsorbed foreign substances are settled quickly and the purity of the surface is highly maintained, the re-dispersion possibility of the foreign substances is further lowered. Since the liquid is swirled, the surface of the liquid does not freeze even at a temperature below the freezing point. Rather, when a liquid having a lower temperature and a lower vapor pressure is used, efficiency in collecting ultrafine particles in the inflow air that is repelled by the reaction against the vapor pressure is improved. The natural vaporization occurring on the surface of the liquid has a slight natural humidification effect. Since an evaporation residue is accelerated and settled due to Ekman transport, the re-dispersion possibility of the evaporation residue is extremely low.

When the center of the liquid swirl comes into contact with the rotating body, the rotating body forcibly mixes the inflow air with the liquid. Thus, the collection efficiency is high, but the generated noise is high. In contrast, when the center of the liquid swirl does not come into contact with the rotating body, no noise is generated, and the noise of the rotating body is also blocked by the liquid. Therefore, there is almost no noise. As a result, it is possible to use a highly efficient wet type air purifier even in quiet places such as homes, indoors, and office spaces.

Since the present disclosure is configured to form a conical portion of a centrifugal dust collector as a liquid swirl, the dust collection efficiency is high even if a swirling flow is not strong. It is possible to operate the air purifier with reduced noise and to lower the re-dispersion possibility of collected dust significantly. In addition, a rotational force in a middle portion and an upper portion of the liquid is relatively low compared to that in a lower portion of the liquid which directly receives the rotational force. As a result, a centrifugal force acts diagonally downward in the middle and upper portions of the liquid and the centrifugation helps settlement of pollutants.

Lorenz's force is a force that acts even on units of one atom. In the double swirl type air purifier, when pollutants bounce off from the center, it is difficult to exactly determine the traveling direction of the pollutants, but the pollutants are trapped within the liquid swirl in all directions. Therefore, when the electromagnetic force forming part is located at the bottom of the guide part and is effectively used, it is possible to collect pollutants in units of one atom.

Moreover, since fine dust has a high content of heavy metals, when the magnetic material is placed within the liquid contained in the lower portion of the dust collector and the liquid swirl is generated, an electromagnetic induction phenomenon occurs. Thus, it is possible to expect the effect of sterilizing the liquid without direct electrolysis of water. In the centrifugal dust collector, since Lorentz's force is added, it is possible to provide excellent air purification ability compared to the conventional wet type dust collectors.

DETAILED DESCRIPTION

Hereinafter, a preferred embodiment of the present disclosure will be described in detail with reference to the accompanying drawings.

For reference, among the configurations of the present disclosure to be described below, the above-described prior art will be referred to for configurations identical to the prior art, and a separate detailed description will be omitted.

Figure 1:
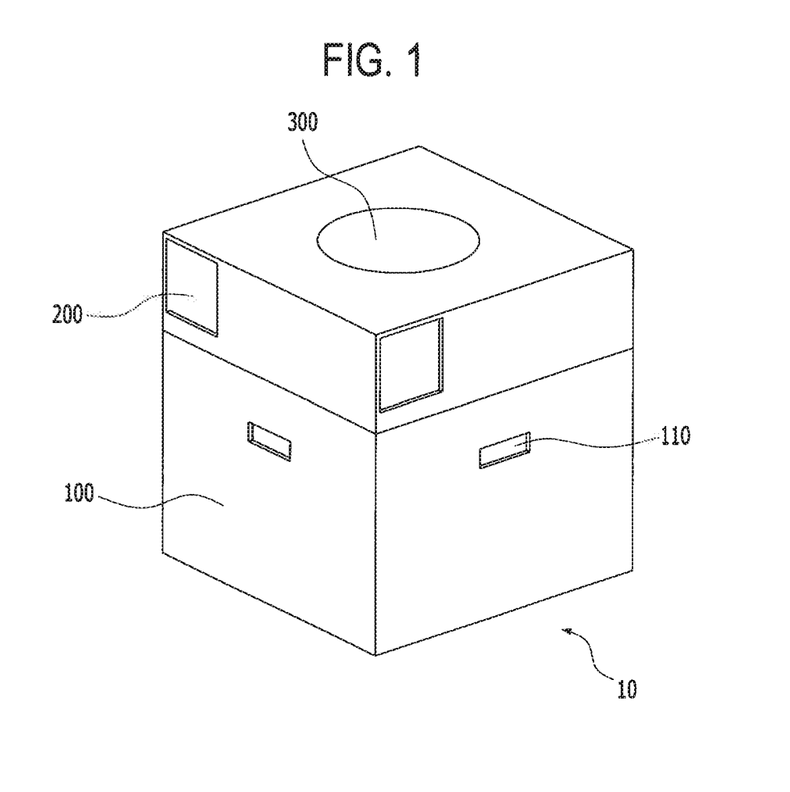
FIG. 1 is a perspective view illustrating a double swirl type air purifier according to one embodiment of the present disclosure.
Figure 2A:
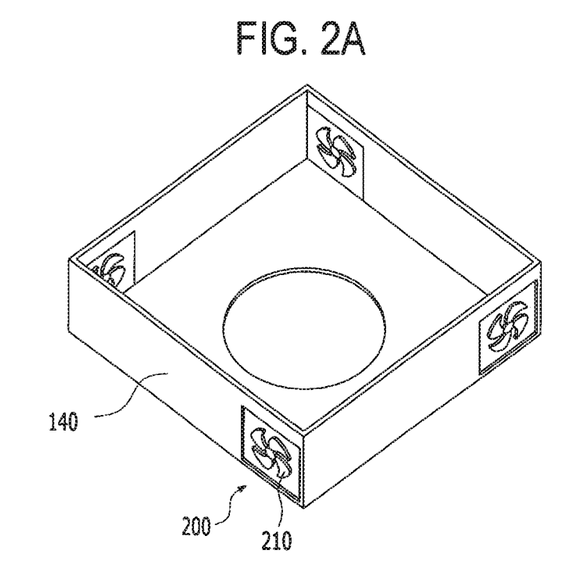
FIGS. 2A and 2B are exploded views illustrating a cover of the double swirl type air purifier according to one embodiment of the present disclosure.
Figure 2B:
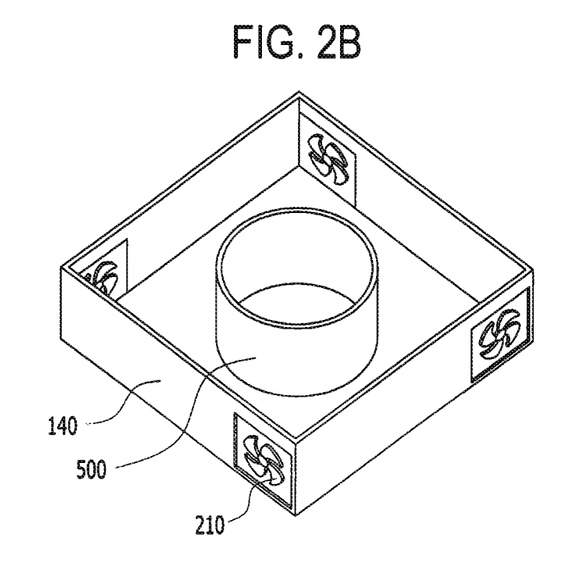

FIG. 1 is a perspective view illustrating a double swirl type air purifier according to one embodiment of the present disclosure. FIGS. 2A and 2B are exploded views illustrating a cover of the double swirl type air purifier according to one embodiment of the present disclosure.

As illustrated in FIGS. 1, 2A, and 2B, the double swirl type air purifier 10 according to one embodiment of the present disclosure includes a main body 100, a suction part 200 located on one side of the main body, a discharge part 300, and a rotation part 400.

The main body 100 is a reservoir containing a liquid for purifying an inflow air in the double swirl type air purifier 10. An upper portion of the main body 100 is opened in order to allow a user of the double swirl type air purifier 10 according to one embodiment of the present disclosure to introduce the liquid into the main body 100. A separate cover 140 is provided so as to cover the opened upper portion of the main body 100. In addition, a receiving groove 410 is formed at a central position of a lower surface of the main body 100 so as to accommodate the rotation part 400 to be described later. The remaining portion of the lower surface may be closed. The receiving groove 410 according to one embodiment of the present disclosure may be defined by a cylindrical protrusion protruding upward. In this case, the receiving groove 410 is located in a lower surface of the rotation part 400 to be described later. Since liquid is accommodated in a lower end portion of the main body 100 as described above, dust collection efficiency can be improved even if an external swirling flow 211 to be described later is not strong. It is possible to configure an air purifier with low noise.

In one embodiment of the present disclosure, the rotation part 400, which will be described later, is installed on a bottom of the main body 100 at a center (not necessarily located at the center) with a space interposed between the bottom and the rotation part 400. A centrifugal sedimentation structure, a filter, a strainer, or a liquid exchange device may be installed on the bottom surface at the location of the receiving groove 410.

Figure 3:
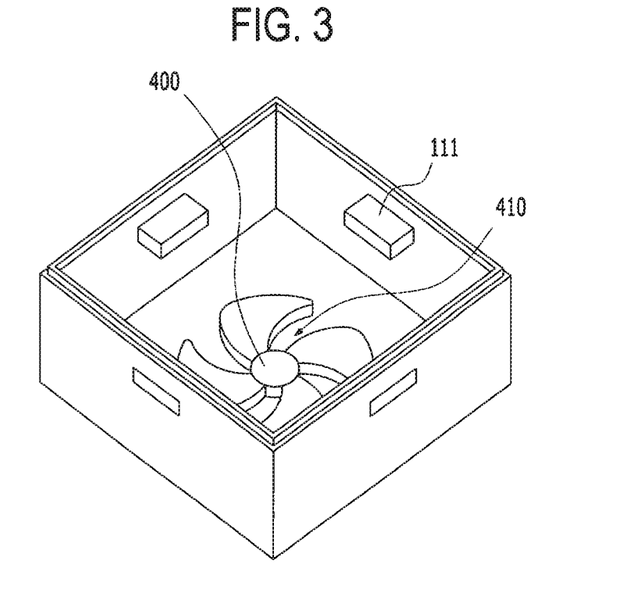
FIG. 3 is an exploded view illustrating a lower portion of a main body of the double swirl type air purifier according to one embodiment of the present disclosure.

FIG. 3 is an exploded view illustrating a lower portion of the main body of the double swirl type air purifier according to one embodiment of the present disclosure.

Referring to FIG. 3, in the main body 100 according to one embodiment of the present disclosure, the rotation part 400 is installed at a position corresponding to a predetermined height or higher from the bottom of the main body 100. The main body 100 may include a centrifugal sedimentation structure, a filter, a strainer, or a liquid exchange device in the space between the rotation part 400 and the bottom of the main body 100.

In another embodiment of the present disclosure, the main body 100 may further include an oil filter or a discharge prevention jaw or structure, which prevents the liquid from spilling when a strong impact is applied to the air purifier or when the main body 100 is overturned.

The suction part 200 is a passage which is located at one side of the main body 100 of the double swirl type air purifier 10 so as to suction external air into the main body 100.

In the double swirl type air purifier 10 according to one embodiment of the present disclosure, the suction part 200 may be located on one side of the upper portion of the main body 100, through which the inflow air is suctioned. It is preferable that the suction part 200 is located above the height of the liquid accommodated in the lower end portion of the main body 100.

Figure 5A:
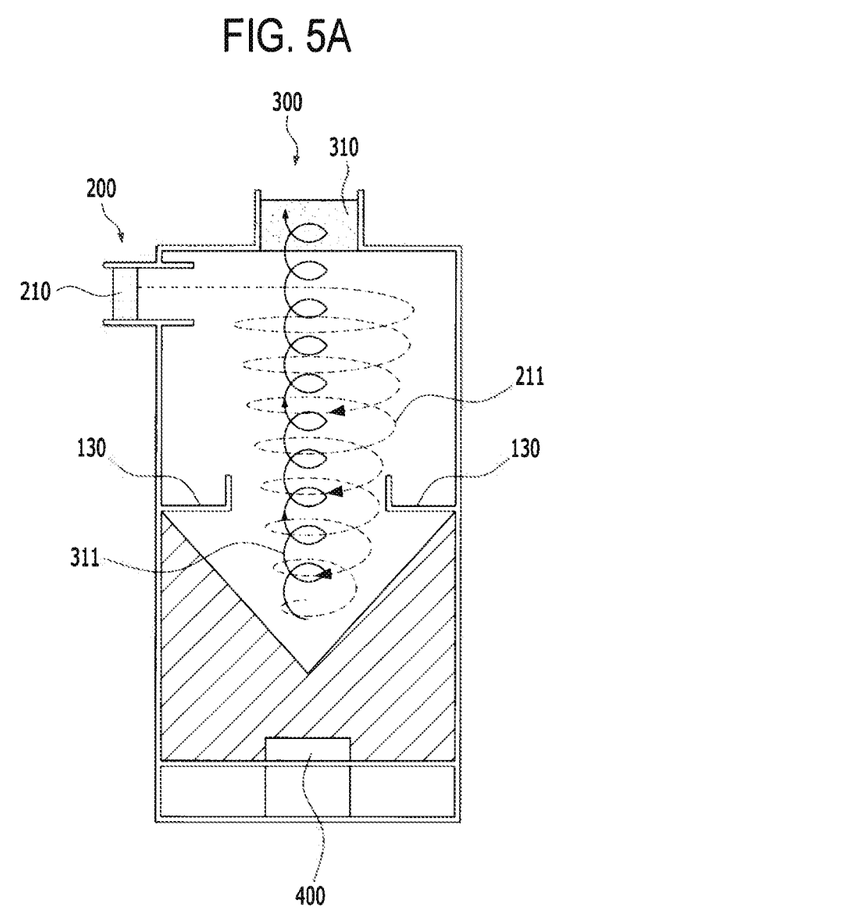
FIG. 5A is a schematic view illustrating the inside of a basic double swirl type air purifier according to one embodiment of the present disclosure.

FIG. 5A is a schematic view illustrating an inside of a basic double swirl type air purifier according to one embodiment of the present disclosure.

The suction part 200 according to one embodiment of the present disclosure may include a separate acceleration part 210 which is configured to raise a speed of the inflow air and generate a swirling air flow inside the main body 100. For example, the acceleration part 210 may be an air suction device such as a turbo fan or a compressor and formed inside or at one side of the suction part 200. The turbo fan as the acceleration part 210 may include a fan and a compressor. Only the compressor may be used as the air suction device. In order to achieve the advantages of the double swirl type air purifier and Ekman transport effectively, it is also preferable that the inflow air is formed as a swirling flow. The swirling flow means descending air flow (hereinafter, referred to as "external swirling flow 211") which moves from the top to the bottom of the main body 100. The air suction device, unlike that of the conventional cyclone dust collector, does not require as much power as that needed to generate an external swirling flow of high speed and high pressure. Therefore, it is possible to implement the air purifier with low noise.

In one embodiment of the present disclosure, when it is necessary to re-suction and use a part of outflow air, the suction part 200 may be configured such that two or more main bodies 100 are coupled to each other, a suction port is provided at the upper side thereof, and a fan is installed in the suction port so as to form the swirling flow which is bidirectionally divided while flowing downward. Two swirling flows formed by each of the inflow air may move upward to be discharged through each of two discharge parts 300 coupled to each of the two main bodies 100.

The suction part 200 according to one embodiment of the present disclosure may further include a filter, a cooler, and an air volume adjustment device. The air volume adjustment device may have a shape of a throttle.

Referring to FIG. 2A, the discharge part 300 may be configured in various forms. The discharge part 300 may be a passage which is located at a predetermined position of the main body 100 and configured to discharge the outflow air introduced from the main body 100.

In the double swirl type air purifier 10 according to one embodiment of the present disclosure, the discharge part 300 and/or a guide part 500 may include an outflow air filter 310 detachably or integrally coupled to the discharge part 300 and/or the guide part 500.

The outflow air filter 310 may be provided inside the discharge part 300 and/or the guide part 500 which is detachably or integrally coupled to the discharge part 300 and/or the guide part 500 so as to purify the outflow air introduced from the main body 100. Herein, the outflow air filter 310 may refer to an air filter structure capable of purifying residual particles in the outflow air, which forms an air swirl (hereinafter, referred to as "internal swirling flow") moving from the bottom to the top in the main body 100. The outflow air filter 310 may have a cylindrical structure. In addition, the outflow air filter 310 may be fastened to be detachably attached to the guide part and include various types of filters (e.g., a dehumidification filter, an oil filter, a High-Efficiency Particulate Air filter, and the like).

More specifically, the outflow air filter 310 may be installed inside the discharge part 300 for appearance. However, when applied to an industrial field, the outflow air filter 310 may be installed outside the discharge part 300 according to the ease of replacement and the role of the filter so that the efficiency of using the air purifier can also be improved.

In one embodiment of the present disclosure, an electromagnetic force forming part to be described later may be coupled to a lower end portion of the outflow air filter 310 which is provided inside the discharge part 300 and/or the guide part 500. The electromagnetic force forming part 110 may form an electromagnetic field that affects the air. The electromagnetic force forming part may include a conducting wire, a permanent magnet, an electromagnet (using a ferromagnetic core in a coil, a solenoid, and an annular inductor), a coil, a solenoid, an inductor, an electric magnet, a variable magnet, and the like.

In addition, the positions and number of air suction devices in the suction part 200 and the positions and number of discharge parts 300 may be variously selected.

Figure 7:
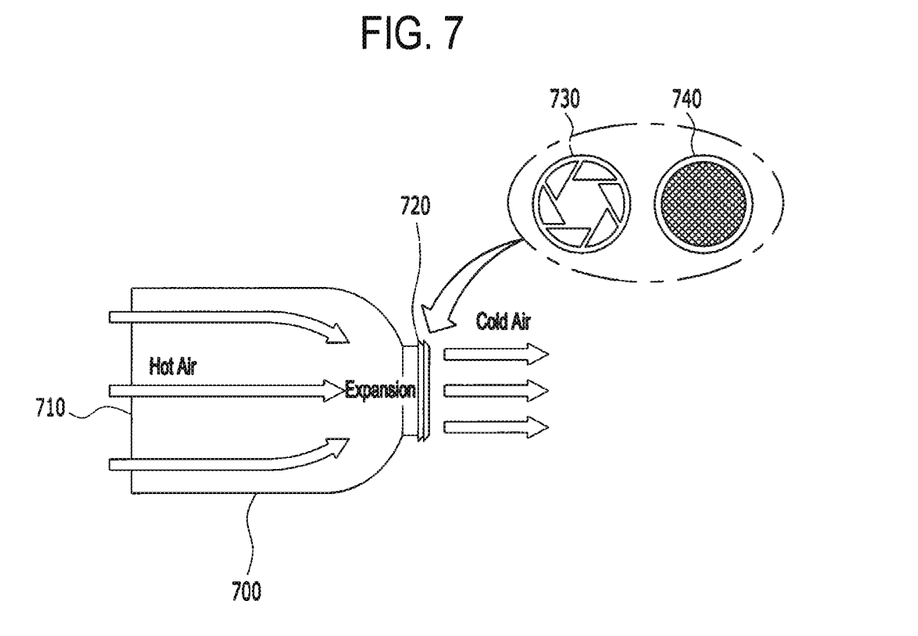
FIG. 7 is an exploded view illustrating a cross-sectional area adjustment part of the double swirl type air purifier according to one embodiment of the present disclosure in a disassembled state.

FIG. 7 illustrates a cross-sectional area adjustment part 700 according to one embodiment of the present disclosure.

In one embodiment of the present disclosure, the discharge part 300 may include the cross-sectional area adjustment part 700, which is detachable from the discharge part 300. The cross-sectional adjustment part 700 includes an air inlet 710 configured to adjust an outflow speed of the outflow air and a cylindrical air outlet 720 through which a receiving groove is formed. The cross-sectional area adjustment part 700 may change a temperature of the outflow air by adjusting a moving speed of the outflow air. The cross-sectional area adjustment part 700 may have a bottleneck structure as illustrated in FIG. 7, or may have a circular tube shape having opened ends at both sides and including the air volume adjustment device.

More specifically, when an amount of the outflow air is set to be smaller than an amount of the inflow air (for example, when air is passed through a bottleneck shaped tube with a large size inlet and a small size outlet), cold air comes out from the air outlet 720 due to Joule Thompson effect. When sizes of the air inlet and the air outlet are reversed, warm air is discharged.

In one embodiment of the present disclosure, the cross-sectional area adjustment part 700 may further include the air volume adjustment device 730 (e.g., a throttle) capable of adjusting the amount of the outflow air or the inflow air and/or a dehumidification filter 740 so as to remove moisture by cooled air.

In one embodiment of the present disclosure, the suction part may be configured to adjust the amount of air more freely by installing a throttle or the like as the air volume adjustment device 730 in the air outlet 720 of the cross-sectional area adjustment part 700 which has a cylindrical shape rather than a bottleneck shape. In this case, since a bottleneck phenomenon occurs in the air flow, the same cooling effect as the circular tube having the bottleneck structure at one side can be generated. In addition, when the air moves and undergoes the bottleneck phenomenon, condensation may occur due to rapid cooling. In order to remove the moisture generated due to the condensation phenomenon, the dehumidification filter 740 may be installed at a position where the inflow air or the outflow air can pass after passing through the air volume adjustment device. Water droplets condensed through the dehumidification filter 740 may flow to the liquid accommodated in the lower end portion of the main body 100. Accordingly, the double swirl type air purifier according to one embodiment of the present disclosure may be an air purifier capable of dehumidifying air. In another embodiment of the present disclosure, the discharge part 300 of the double swirl type air purifier according to one embodiment of the present disclosure may include a direct dehumidification device, a dehumidification filter, or a cooler so as to adjust humidity. In addition, when the double swirl type air purifier according to one embodiment of the present disclosure further includes the cross-sectional area adjustment part 700, it is possible to adjust the temperature of the inflow air and the outflow air. Thus, it is possible to supply cold air or warm air. Moreover, when the cross-sectional area adjustment part 700 is installed in the suction part such that the inflow air is cooled, Brownian motion of inflow particles may be reduced so that the collection rate of fine dust can be increased.

The cross-sectional area adjustment part 700 may also be detachably fastened to the suction part 200 in the same manner as described above.

The rotation part 400 may include a device that is located in a lower portion of the main body 100 and rotates the liquid (e.g., a motor including a fan).

Referring to FIG. 5A, in one embodiment of the present disclosure, one or more rotation parts 400 may be located in the liquid accommodated in the main body 100 to swirl the liquid accommodated in the main body 100, and to increase contact area per unit time between the liquid and the inflow air forming the external swirling flow by the suction pressure of the suction part 200, whereby the air is purified by allowing particles, such as impurities, fine dust, and heavy metals contained in the inflow air, to be collected in the liquid. In addition, in another embodiment of the present disclosure, the rotation part can be driven with low noise by adjusting the rotation of the rotation part (e.g., the rotational speed (rpm)) such that the center of the liquid swirl does not come into contact with the rotation part. To this end, a rotational force may be lowered by decreasing a voltage supplied to the rotation part or increasing a resistance of the rotation part to adjust electric power to be used.

Figure 6:
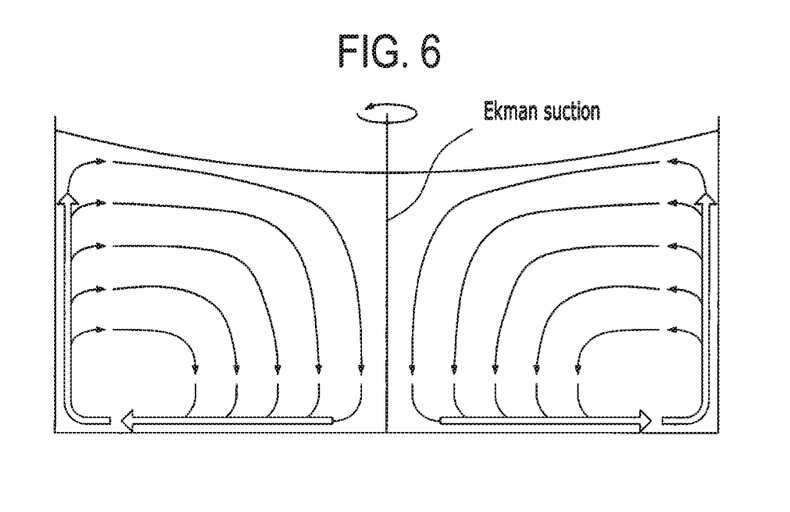
FIG. 6 is a schematic view illustrating a liquid flow when the double swirl type air purifier according to one embodiment of the present disclosure is driven.

FIG. 6 is a schematic view illustrating liquid flow when the double swirl type air purifier according to one embodiment of the present disclosure is driven.

More specifically, referring to FIG. 6, when the rotation part 400 is located in the liquid in the main body 100 and driven, the liquid can be swirled. When the liquid is swirled, a surface of the liquid becomes a conical shape in which a central height is low, and thus the surface area become wider. Since the surface of the liquid rotates at a high speed, the contact area with the external swirling flow becomes wider than that in the case in which the liquid is not swirled. Therefore, it is relatively easy for the liquid to collect fine particles contained in the inflow air, and thus the efficiency of the air purifier is improved.

As another effect, when the rotational speed of the rotation part 400 is increased and the swirling speed of the liquid is increased, the amount of particles processed on the surface of the liquid per unit time by centrifugal force can be increased, and thus the collection efficiency can be increased. In addition, it is possible to prevent the formation of a dust film on the surface of the liquid by causing pollutants to be rapidly settled into the liquid such that the pollutants collected on the liquid surface do not stagnate on the surface of the liquid.

In one embodiment of the present disclosure, two or more rotation parts 400 are included in the main body 100, and each of rotation parts 400 may form multiple liquid swirls, or the rotation part 400 may rotate the liquid around an axis extending in a diagonal direction rather than a vertical direction.

In one embodiment of the present disclosure, the double swirl type air purifier may further include a controller configured to adjust the rotational speed of the rotation part 400. When the double swirl type air purifier is driven in a state in which the RPM of the rotation part is adjusted by the controller such that the center of the liquid swirl is located at a predetermined height of the rotation part, it is possible to significantly reduce driving noise compared to the case in which the center height of the liquid swirl comes into contact with the rotation part. In another embodiment of the present disclosure, it is possible to drive the rotation part in a state in which the RPM of the rotation part is adjusted by the controller such that the center height of the liquid swirl is brought into contact with the rotation part, whereby the air purification efficiency can be improved drastically.

Figure 5B:
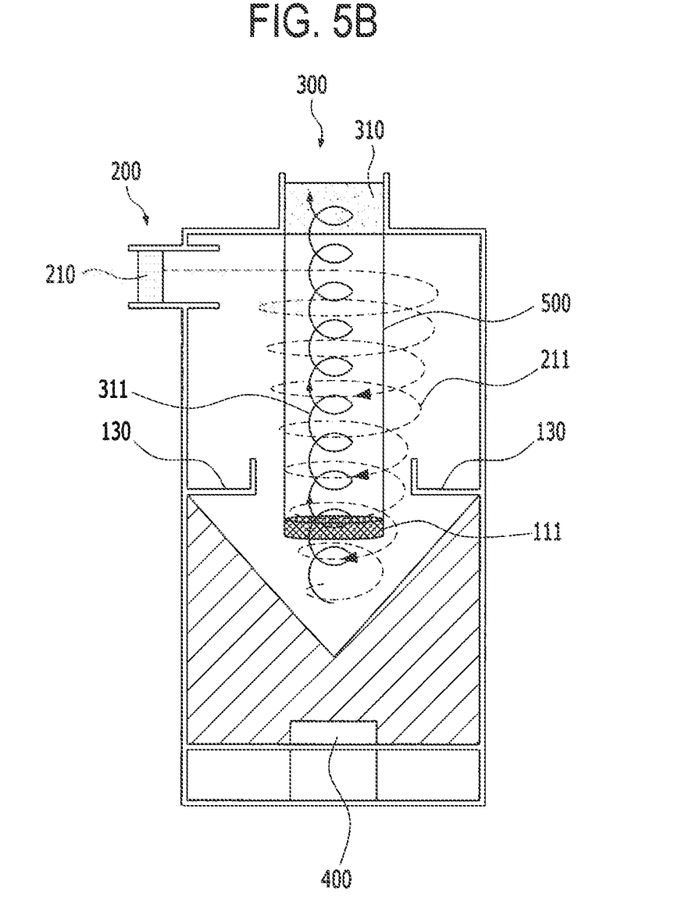
FIG. 5B is a schematic view illustrating the inside of the double swirl type air purifier including a guide part according to one embodiment of the present disclosure.

FIG. 2B is a perspective view illustrating a cover 140 of the main body 100 including a guide part. FIG. 5B is a schematic view illustrating the inside of the double swirl type air purifier including the guide part according to one embodiment of the present disclosure.

Referring to FIG. 2B, in one embodiment of the present disclosure, the cover 140 of the main body 100 may further include the guide part 500, which is detachable from the discharge part 300 and protrudes from the discharge part into the main body. In another embodiment of the present disclosure, the guide part 500 may have a cylindrical shape with an opened lower end.

Referring to FIG. 5B, in one embodiment of the present disclosure, the guide part 500 is configured to prevent the external swirling flow 211, which is a descending air flow formed by the inflow air introduced through the suction part 200, and the internal swirling flow 311, which is a rising air flow formed from the bottom toward the top in the main body 100 by the outflow air, from which particles, such as fine dust and the like, have been removed by being brought into contact with the liquid accommodated in the main body 100 even during low-speed and low-noise operation or separation of light gas, whereby it is possible to improve the air purification efficiency.

In one embodiment of the present disclosure, the guide part 500 may include multiple circular rod-shaped filters having a small radius. The guide part 500 may be disposed along a periphery of the discharge part 300 at regular intervals. In another embodiment of the present disclosure, the guide part 500 may be formed in a cylindrical mesh structure or in the form of a bamboo blind screen.

More specifically, the inflow air, from which the fine particles have been removed by being brought into contact with the swirled liquid, forms the internal swirling flow 311 which is a rising air flow having a smaller radius and slower speed than the external swirling flow, due to reaction with the liquid swirl. However, unlike the conventional cyclone dust collector, the air purifier does not form a high-speed and high-pressure swirl, and thus there is a possibility that the internal swirling flow is mixed with the external swirling flow 211. By fastening the guide part 500 in order to prevent this, it is possible to improve the efficiency of the air purifier.

Figure 4:
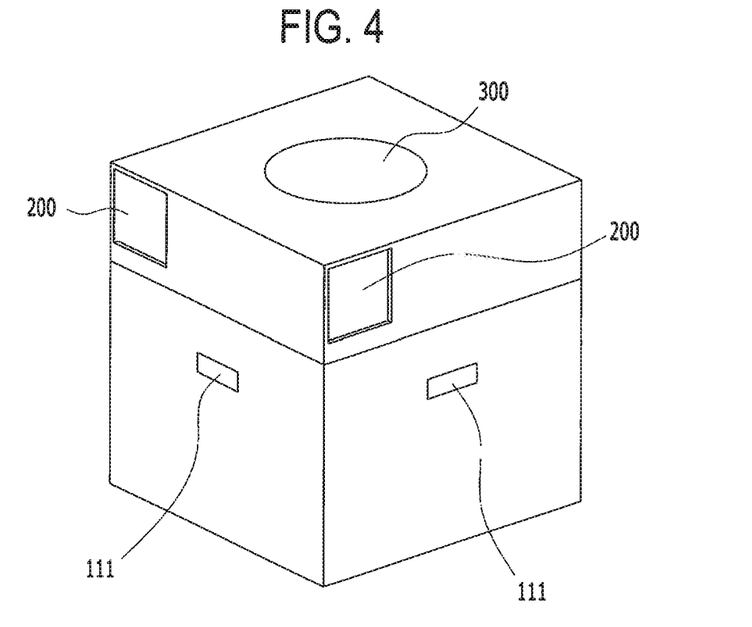
FIG. 4 is a perspective view illustrating the double swirl type air purifier including a permanent magnet according to one embodiment of the present disclosure.

FIGS. 4 and 5B are perspective views illustrating the double swirl type air purifier including a permanent magnet according to one embodiment of the present disclosure.

In one embodiment of the present disclosure, the main body 100 may further include an electromagnetic force forming part 110 disposed at a predetermined position of the main body 100.

The predetermined position may mean a position at which the electromagnetic force forming part 110 is coupled to a portion of the main body 100, in a portion that is immersed in the liquid accommodated in the main body 100, or may mean an arbitrary position at which the magnetic force forming part 110 can be coupled to the main body, on an inner wall or an outer wall of the main body 100 outside the liquid. In addition, as illustrated in FIG. 5B, the electromagnetic force forming part 110 may be configured such that a permanent magnet 111 is coupled to the lower end of the guide part 500.

The electromagnetic force forming part 110 is disposed in a portion of the lower portion of the main body 100 so as to be immersed in the liquid accommodated in the lower portion of the main body 100. The electromagnetic force forming part 110 includes at least one permanent magnet 111, an electromagnet (in which a ferromagnetic material such as iron is used as a magnetic core in a coil, solenoid, annular inductor, etc.), a coil, and the like such that an electric field or a magnetic field can be formed. Here, the electric field may be an induced electric field, and the magnetic field may be an induced magnetic field. Therefore, when the liquid swirl is generated by the rotation part 400 and when an electromagnetic force is generated due to the motion of heavy metal particles contained in the liquid and the magnetic field of the electromagnetic force forming part 110, the magnetic field causes the heavy metal particles, such as fine pollutants, to be attracted to or to move away from the center of the liquid swirl by Lorentz's force. At the same time, the fine pollutants are caused to rapidly settle from the surface of the liquid into the liquid. This prevents or eliminates the formation of a film on the surface of the liquid (e.g., a film formed by accumulated fine dust particles), and helps to keep the surface of the liquid clean. As a result, it is possible to improve the efficiency of the air purifier by preventing degradation of the ability of the liquid for collecting particles. A conductor, a coil, and a solenoid generate the electric field. A permanent magnet, an electromagnet, an electric magnet, and a variable magnet generate a magnetic field.

In one embodiment of the present disclosure, the main body 100 may further include a cooling part (not illustrated) located inside and/or outside the liquid accommodated in the lower portion of the main body 100 so as to lower the temperature of the internal air of the main body 100 and the temperature of the liquid. In addition, the cooling part (not illustrated) may be included within the suction part 200 so as to directly lower the temperature of the inflow air, or may be included within the guide part so as to directly lower the temperature of the outflow air.

Particles contained in the inflow air generally perform Brownian motion in the air. Conventional air purifiers have disadvantages in that they are particularly vulnerable to ultrafine dust and smaller particles due to the Brownian motion of the particles, and have difficulty in maintaining performance. Since Brownian motion of particles is proportional to temperature $$\left(\sqrt{\Delta x^2} = \sqrt{kT}\,\frac{\sqrt{t}}{\sqrt{3\pi\mu r}}\right),$$

when the temperature is lowered, Brownian kinetic force of the particles can be lowered. Accordingly, the cooling part (not illustrated) may function to lower Brownian kinetic force by lowering the temperature of the inflow air and the temperature of the liquid inside the main body 100. In addition, when the temperature of the liquid is lowered, a vapor pressure of the liquid is lowered. Since the vapor pressure of the liquid corresponds to a force to repel Brownian particles from the surface of the liquid, when the vapor pressure is lowered, the ability of collecting particles such as fine dust in the liquid is improved. Therefore, when the temperature of the inflow air and the temperature of the liquid are lowered due to the cooling part (not illustrated), the efficiency of the air purifier can be improved. That is, when the inflow air is directly cooled by the cooling part (not illustrated), or Joule Thompson effect (due to the principle of Joule Thompson effect, when the size of the discharge part is reduced compared to the size of the suction part, cold air flows out, or reversely, warm air flows out) is exerted through the cross-sectional area adjustment part 700 described above, Brownian motion of the dust can be reduced and the rate of collecting ultrafine dust can be increased.

In one embodiment of the present disclosure, it is possible to increase the rate of collecting ultrafine dust and smaller particles using, as the liquid accommodated in the main body 100, a liquid having a lower vapor pressure than water at the same temperature (e.g., diphenyl ether or a mixture thereof), or the like.

Figure 5C:
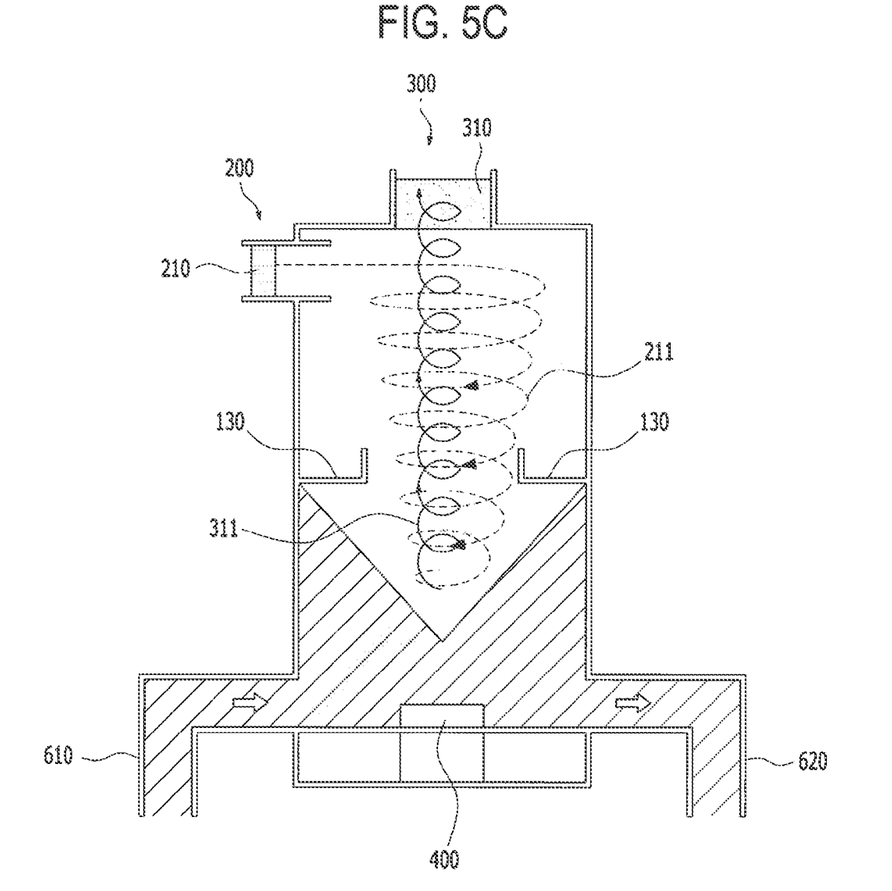
FIG. 5C is a schematic view illustrating a basic double swirl type air purifier including a liquid suction part and a liquid discharge part according to one embodiment of the present disclosure.

FIG. 5C is a schematic view illustrating a basic double swirl type air purifier including an internal filter 130, a liquid suction part, and a liquid discharge part according to one embodiment of the present disclosure.

Referring to FIG. 5C, in one embodiment of the present invention, the main body 100 may further include at least one internal filter 130 coupled to the main body 100 and installed on the inner surface of the main body 100 which is immersed in the liquid.

The internal filter 130 is fastened to the inner wall of the main body 100 at a predetermined height from the lower end portion of the main body 100, and is located below the surface of the liquid accommodated in the main body 100 so as to prevent the rising of the fine particles that are not affected by a magnetic force among the particles collected in the liquid, thereby effectively preventing re-dispersion of particles settled into the liquid.

More specifically, in one embodiment of the present disclosure, the internal filter 130 may include a strainer and the like, in which the impurities can be trapped while the liquid is moving (filtering action). Since the internal filter 130 is made of an elastic plastic material, it is easy to remove the impurities such as foreign substances and to semi-permanently reuse the internal filter 130 after washing or brushing. In more detail, as illustrated in FIG. 6, a flow speed of the liquid is faster in an outer portion of the liquid than in an inner portion of the liquid due to the rotational force, and thus Ekman suction occurs in the center of the liquid. Accordingly, the liquid located on a bottom wall and an inner wall of the main body rises more rapidly to fill an empty space in the center of the liquid. Thus, the fine particles, which are not affected by the electromagnetic force, rise to the surface of the liquid by this rising flow speed. The main body 100 according to one embodiment of the present disclosure may include the internal filter 130, which can be fastened to the inner wall of the main body at the predetermined height from the lower end portion of the main body 100 in order to prevent re-dispersion of such fine particles.

Referring to FIG. 5C, in one embodiment of the present disclosure, the main body 100 may further include a liquid suction part 610 located at one side of the lower portion of an outer circumferential surface of the main body 100 so as to introduce the liquid, and a liquid discharge part 620 disposed at the other side of the lower portion of the outer circumferential surface of the main body 100 so as to discharge the liquid containing the impurities.

More specifically, the liquid suction part 610 formed in a predetermined lower surface of the main body 100 may form a flow path through which the liquid is movable, and the liquid introduced through the flow path is movable again to the liquid discharge part 620 after collecting the particles such as the impurities. In addition, in order to ensure more effective movement of liquid, the liquid discharge part 620 may have a slope that gently descends toward the outside. The liquid is capable of being effectively discharged due to this slope. The liquid collecting the particles is capable of being maintained in a clean state as it continuously moves along the liquid discharge part 620. Thus, it is possible to use the liquid in a place where it is required to operate the air purifier for 24 hours.

In addition, in one embodiment of the present disclosure, the main body 100 of the double swirl type air purifier 10 may include a liquid further containing a surfactant capable of improving a settlement rate of the collected particles.

Therefore, according to the present disclosure, it is possible to significantly improve a filtration performance of the air purifier in a wet manner of collecting the dust and the impurities and purifying the air by bringing the air into contact with the liquid. Thus, it is possible to maintain a comfortable environment in the workplace by turning the air into a clean state.

While the present disclosure has been described above with reference to specific matters, such as specific components, restricted embodiments, and drawings, these are provided only to help in a more general understanding of the present disclosure. The present disclosure is not limited to the embodiments described above, and various modifications and variations can be made by a person of ordinary skill in the art to which the present disclosure belongs.

Therefore, the spirit of the present disclosure should not be limited to the embodiments described above, and it is intended that not only the appended claims, but also all things equivalent to or equivalently changed from the claims, be considered to fall within the spirit of the present disclosure.

What is claimed is:

1. An air purifier comprising:
a liquid for purifying an inflow air;
a main body configured to accommodate the liquid;
a suction part located at one side of the main body and configured to suction the inflow air to be swirled by an inflow pressure of the suction part; and
a discharge part located at a predetermined position of the main body and configured to discharge an outflow air introduced from the main body,
wherein the main body includes a rotation part located at a lower portion of the main body and configured to rotate the liquid to be swirled,
wherein a contact area per unit time between the liquid swirled by the rotation part and the inflow air swirled by the inflow pressure of the suction part is increased so as to improve air purification efficiency,
wherein the main body further includes a cooling part located inside and/or outside a liquid accommodated in the lower portion of the main body and configured to lower a temperature of the liquid, and
wherein a rate of collecting fine particles is improved by reducing a vapor pressure of the liquid and a repulsive force of the fine particles directed to a surface of the liquid from the inflow air.

2. The air purifier of claim 1, wherein the suction part includes an acceleration part disposed at an inlet of the suction part and configured to raise a speed of the inflow air such that an air swirl is generated.

3. The air purifier of claim 1, wherein the discharge part includes a guide part protruding from the discharge part toward an inside of the main body so as to prevent the inflow air and the outflow air from being mixed with each other.

4. The air purifier of claim 3, wherein the guide part includes an outflow air filter detachably fastened to the guide part so as to purify the outflow air introduced from the main body.

5. The air purifier of claim 1, wherein the main body further includes an electromagnetic force forming part coupled to a predetermined position of the main body or a guide part, and
wherein the electromagnetic force forming part includes a conductive wire or a magnetic material capable of forming an electric field or a magnetic field such that a rate of collecting fine pollutants is increased.

6. An air purifier comprising:
a liquid for purifying an inflow air;
a main body configured to accommodate the liquid;
a suction part located at one side of the main body and configured to suction the inflow air to be swirled by an inflow pressure of the suction part; and
a discharge part located at a predetermined position of the main body and configured to discharge an outflow air introduced from the main body,
wherein the main body includes a rotation part located at a lower portion of the main body and configured to rotate the liquid to be swirled,
wherein a contact area per unit time between a liquid swirl generated by the rotation part and the inflow air swirled by the inflow pressure of the suction part is increased so as to improve air purification efficiency,
wherein the suction part includes a cross-sectional area adjustment part, which is detachable from the suction part and configured to increase a speed of the inflow air and to lower a temperature of the inflow air, and
wherein the cross-sectional area adjustment part further includes an air volume adjustment device capable of adjusting a cross-sectional area of the suction part through which the inflow air passes such that a rate of collecting fine pollutants is improved by adjusting a moving speed of the inflow air or the outflow air and cooling down the inflow air or the outflow air.

7. An air purifier comprising:
a liquid for purifying an inflow air;
a main body configured to accommodate the liquid;
a suction part located at one side of the main body and configured to suction the inflow air to be swirled by an inflow pressure of the suction part; and
a discharge part located at a predetermined position of the main body and configured to discharge an outflow air introduced from the main body,
wherein the main body includes a rotation part located at a lower portion of the main body and configured to rotate the liquid to be swirled,
wherein a contact area per unit time between a liquid swirl generated by the rotation part and the inflow air swirled by the inflow pressure of the suction part is increased so as to improve air purification efficiency, and
wherein the rotation part is configured to adjust a rotation such that a center of the swirled liquid is not brought into contact with the rotation part, thereby operating with low noise.

* * * * *